(12) United States Patent
Engman et al.

(10) Patent No.: US 12,172,023 B2
(45) Date of Patent: Dec. 24, 2024

(54) DATA CHANNEL SELECTION AND TIMELINE NAVIGATION IN A CARDIAC MONITORING SYSTEM

(71) Applicant: WEST AFFUM HOLDINGS DAC, Dublin (IE)

(72) Inventors: Zoie R. Engman, Kirkland, WA (US); Jonathan P. Niegowski, Issaquah, WA (US); Laura M. Gustavson, Redmond, WA (US); Pamela F. Breske, Newcastle, WA (US); Angela M. Stewart, Kirkland, WA (US); Steven E. Sjoquist, Lynnwood, WA (US)

(73) Assignee: West Affum Holdings DAC, Dublin (IE)

( * ) Notice: Subject to any disclaimer, the term of this patent is extended or adjusted under 35 U.S.C. 154(b) by 180 days.

(21) Appl. No.: 17/688,627

(22) Filed: Mar. 7, 2022

(65) Prior Publication Data

US 2022/0355123 A1    Nov. 10, 2022

Related U.S. Application Data

(60) Provisional application No. 63/157,520, filed on Mar. 5, 2021.

(51) Int. Cl.
*A61N 1/39* (2006.01)

(52) U.S. Cl.
CPC ......... *A61N 1/3993* (2013.01); *A61N 1/3904* (2017.08)

(58) Field of Classification Search
CPC ............................. A61N 1/3993; A61N 1/3904
(Continued)

(56) References Cited

U.S. PATENT DOCUMENTS

| 3,724,355 A | 4/1973 | Busch et al. |
| 4,583,524 A | 4/1986 | Hutchins |

(Continued)

FOREIGN PATENT DOCUMENTS

| DE | 2005060985 A2 | 6/2007 |
| EP | 2305110 A1 | 4/2011 |

(Continued)

OTHER PUBLICATIONS

Heartstart MRx and XL AED Algorithm—Application Note, Jul. 2001, Edition 2 Philips Healthcare, USA.

(Continued)

*Primary Examiner* — Nadia A Mahmood
(74) *Attorney, Agent, or Firm* — Polsinelli PC

(57) ABSTRACT

Disclosed are a timeline-based navigation feature and a channel selection feature. The timeline-based navigation feature allows the user to visually identify significant events during an episode and quickly navigate the display of data to those significant events. Embodiments of such feature allow a user to quickly see that there is a shock delivered, for example, and click on that part of a timeline navigator to advance the detailed display of data to that point in the episode. The data channel selection feature enables selection of display channel(s) from among a set of available data channels. Embodiments of such feature enable a selection and/or deselection of various channels for display to minimize display of extraneous data and/or to select preferred channels of data for review.

20 Claims, 8 Drawing Sheets

(58) Field of Classification Search
USPC .......................................................... 607/42
See application file for complete search history.

(56) References Cited

U.S. PATENT DOCUMENTS

| | | | |
|---|---|---|---|
| 4,619,265 A | 10/1986 | Morgan et al. | |
| 4,666,432 A | 5/1987 | McNeish et al. | |
| 4,698,848 A | 10/1987 | Buckley | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,429,593 A | 7/1995 | Matory | |
| 5,474,574 A | 12/1995 | Payne et al. | |
| 5,618,208 A | 4/1997 | Crouse et al. | |
| 5,662,690 A | 9/1997 | Cole et al. | |
| 5,708,978 A | 1/1998 | Johnsrud | |
| 5,741,306 A | 4/1998 | Glegyak et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 | 8/2001 | Glegyak et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,450,942 B1 | 9/2002 | Lapanashvili et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,753,759 B2 | 7/2010 | Pintor et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,024,037 B2 | 9/2011 | Kumar | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,527,028 B2 | 9/2013 | Kurzweil et al. | |
| 8,548,557 B2 | 10/2013 | Garstka et al. | |
| 8,560,044 B2 | 10/2013 | Kurzweil et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,706,255 B2 | 4/2014 | Phillips et al. | |
| 8,742,349 B2 | 6/2014 | Urbon et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| 9,265,432 B2 | 2/2016 | Warren et al. | |
| 9,345,898 B2 | 5/2016 | Piha et al. | |
| 9,408,548 B2 | 8/2016 | Volpe et al. | |
| 9,445,719 B2 | 9/2016 | Libbus et al. | |
| 9,454,219 B2 | 9/2016 | Volpe et al. | |
| 9,579,020 B2 | 2/2017 | Libbus et al. | |
| 9,592,403 B2 | 3/2017 | Sullivan | |
| 9,598,799 B2 | 3/2017 | Shoshani et al. | |
| 9,675,804 B2 | 6/2017 | Whiting et al. | |
| 9,757,581 B2 | 9/2017 | Sullivan et al. | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,192,387 B2 | 1/2019 | Brinig et al. | |
| 10,307,133 B2 | 6/2019 | Kaib | |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 2002/0181680 A1 | 12/2002 | Linder et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Vollpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1* | 11/2011 | Kaib | A61B 5/0816 607/5 |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0094604 A1* | 4/2015 | Amann | A61B 5/742 600/510 |
| 2015/0161554 A1 | 6/2015 | Sweeney et al. | |
| 2015/0297135 A1 | 10/2015 | Shoshani et al. | |
| 2015/0328472 A1 | 11/2015 | Sullivan et al. | |
| 2016/0004831 A1 | 1/2016 | Carlson et al. | |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0256104 A1 | 9/2016 | Romem et al. | |
| 2016/0283900 A1 | 9/2016 | Johnson et al. | |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0046682 A1 | 3/2017 | Kumar et al. | |
| 2017/0162840 A1 | 6/2017 | Pendry | |
| 2017/0319862 A1 | 11/2017 | Foshee, Jr. et al. | |
| 2017/0367591 A1 | 12/2017 | Jorgensen | |

(56) References Cited

U.S. PATENT DOCUMENTS

| | | |
|---|---|---|
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030351 A1 | 1/2019 | Sullivan et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0209853 A1 | 7/2019 | Kim et al. |
| 2019/0321650 A1 | 10/2019 | Raymond et al. |

FOREIGN PATENT DOCUMENTS

| | | |
|---|---|---|
| JP | 4320257 A | 3/2005 |
| JP | 5963767 A | 1/2014 |
| JP | 2014526282 A | 10/2014 |
| WO | 98/39061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

\* cited by examiner

DATA CHANNEL SELECTION AND TIMELINE NAVIGATION IN A CARDIAC MONITORING SYSTEM

CROSS-REFERENCE TO RELATED APPLICATIONS

The present application claims the benefit of Provisional Application No. 63/157,520, filed Mar. 5, 2021, entitled "Data Channel Selection and Timeline Navigation in a Cardiac Monitoring System," the entire disclosure of which is hereby incorporated by reference herein for all purposes.

SUMMARY OF THE DISCLOSURE WITH BACKGROUND INFORMATION

When people suffer from some types of heart arrhythmias, the result may be that blood flow to various parts of the body is reduced. Some arrhythmias may even result in a Sudden Cardiac Arrest (SCA). SCA can lead to death very quickly, unless treated, e.g., within 10 minutes Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's Electrical activity. If certain heart arrhythmias are detected, the ICD delivers an electric shock to the heart.

As a further precaution, people who have been identified to have an increased risk of an SCA are sometimes given a Wearable Cardioverter Defibrillator (WCD) system, to wear until the time that their ICD is implanted, or until their cardiac condition no longer puts them in a category for high risk of SCA.

A wearable cardiac defibrillator (WCD) system typically includes a harness, vest, belt, or other garment that the patient is to wear. The WCD system further includes electronic components, such as a defibrillator and electrodes, coupled to the harness, vest, or other garment. When the patient wears the WCD system, the electrodes make electrical contact with the patient's skin, and therefore can help sense the patient's ECG. If a shockable heart arrhythmia (e.g., ventricular fibrillation (VF) or ventricular tachycardia (VT)) is detected from the ECG, then the defibrillator delivers an appropriate electric shock through the patient's body, and thus through the heart. The delivered shock may restart the patient's heart and thus save the patient's life.

Remote monitoring is a rapidly growing field of patient care. As such, devices, such as a WCD system with monitoring capabilities, with connectivity to a remote monitoring product provide a clinical user with the ability to view data acquired by the devices. However, in many cases, these clinical users struggle with an overload of data provided by the devices and are fatigued by this overload. In some cases, these clinical users may ignore (either consciously or subconsciously) the data if it is repeatedly shown to be non-clinically relevant. This can lead to a negative impression of the device, poor opinion of the device manufacturer, and missed opportunities for clinical intervention.

Embodiments of this disclosure implement a timeline-based navigation feature that allows the user to visually identify significant events during an episode and quickly navigate the display of data to those significant events. For example, consider a 10 minute long episode with a shock alarm & shock delivered event. Typical systems for review of episodic data require page-by-page, button-click, or mouse scrolling navigation to advance through the episode from the beginning to the end. Embodiments of the disclosure allow a user to quickly see that there is a shock delivered, for example, and click on that part of a timeline navigator to advance the detailed display of data to that point in the episode.

Other embodiments of the disclosure implement a channel selection feature that allows the user to select one or more data channels for display from among a set of available data channels. For example, some medical monitoring devices are configured to measure and capture multiple simultaneous channels of patient data, such as multiple channels of ECG signals captured using multiple ECG sensors. In such cases, embodiments of the disclosure implement a channel selection feature to enable a selection and/or deselection of various channels for display to minimize display of extraneous data and/or to select preferred channels of data for review.

None of the subject matter discussed in this section is necessarily prior art and may not be presumed to be prior art simply because it is presented in this section. Any reference to any prior art in this description is not, and should not be taken as, an acknowledgment or any form of suggestion that such prior art forms parts of the common general knowledge in any art in any country. Along these lines, any recognition of problems in the prior art discussed in this section or associated with such subject matter should not be treated as prior art, unless expressly stated to be prior art. Rather, the discussion of any subject matter in this section should be treated as part of the approach taken towards solving the particular problems identified. This approach in and of itself may also be inventive.

The summary provided above is intended to introduce a selection of concepts in a simplified form that are further described below in the Detailed Description. This summary is not intended to identify key features of the claimed subject matter, nor is it intended to be used as an aid in determining the scope of the claimed subject matter.

BRIEF DESCRIPTION OF THE DRAWINGS

Embodiments of the disclosure are best illustrated by way of example and not by way of limitation in the figures of the accompanying drawings, briefly described below, in which like reference numerals indicate similar elements.

DETAILED DESCRIPTION OF EMBODIMENTS

Generally described, this disclosure is directed at a Graphical User Interface (GUI) for use with a cardiac monitoring system and that enables data channel selection and direct timeline navigation. While illustrative embodiments are described, it will be appreciated that various changes can be made therein without departing from the spirit and scope of the disclosure. It should also be noted that references to "an embodiment" or "one embodiment" in this disclosure are not necessarily to the same embodiment, and those terms mean at least but not necessarily one.

The following detailed description is structured in two parts. The first part of the disclosure (comprising FIGS. 1-4) describes one exemplary cardiac monitoring system—a Wearable Cardioverter Defibrillator (WCD)—which may be implemented in various embodiments to collect and report on patient cardiac data. The second part of the disclosure (comprising FIGS. 5-9) describes a cardiac monitoring environment in which a graphical user interface is provided that enables data channel selection and direct timeline navigation of the patient cardiac data.

Figure 1:
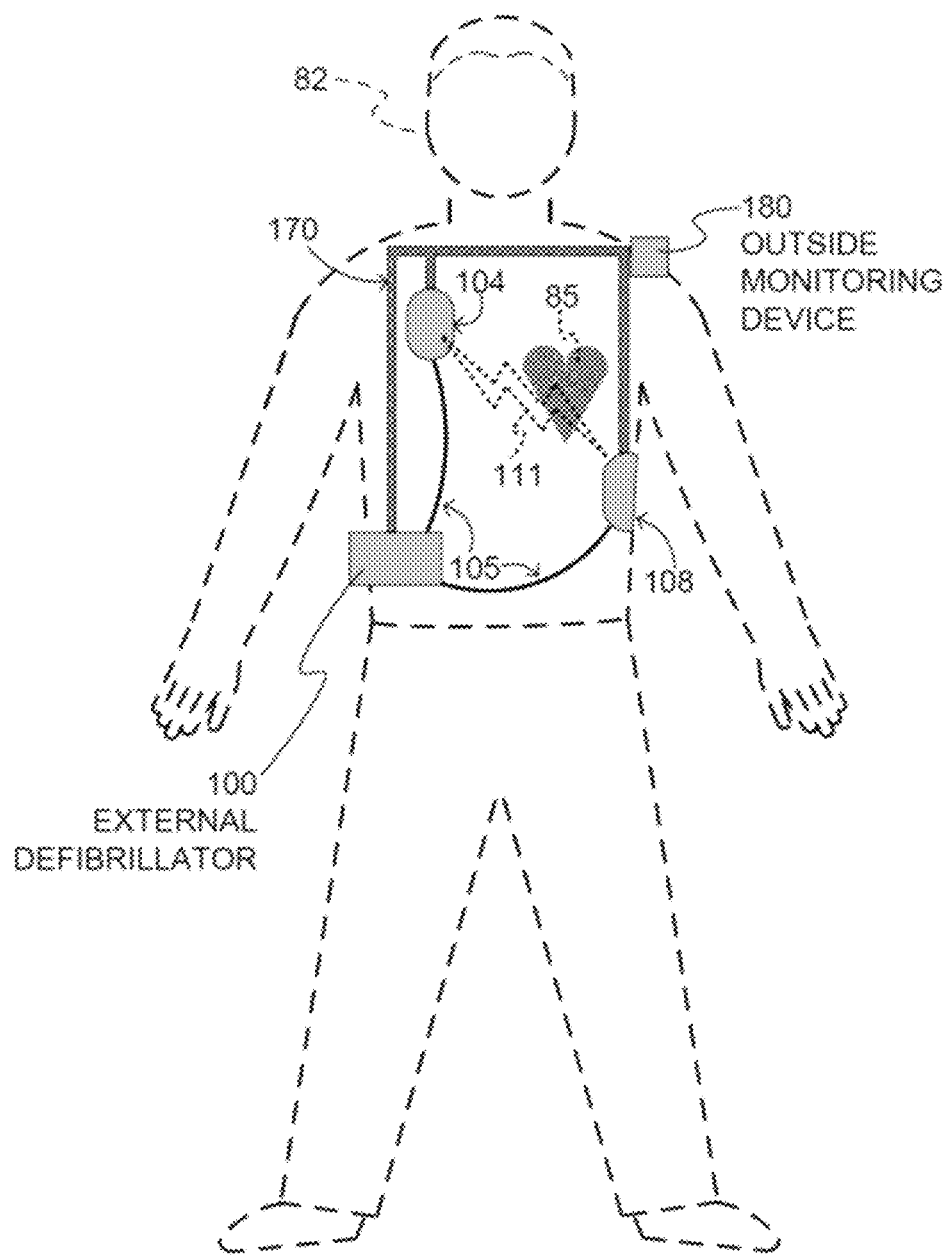
FIG. 1 is a conceptual diagram of a patient wearing an exemplary WCD, made according to embodiments.

Turning now to the first part of the disclosure, FIG. 1 depicts a WCD system being worn by a patient 82, according to embodiments of the disclosure. The WCD described herein is presented as one example of a cardiac monitoring system or device that measures and captures cardiac data (e.g., ECG trace data) for a patient wearing the cardiac monitoring system.

Patient 82 may also be referred to as a person and/or wearer since the patient is wearing components of the WCD system. Patient 82 is ambulatory, which means that, while wearing the wearable portion of the WCD system, patient 82 can walk around and is not necessarily bed ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses and/or again should the WCD continue to detect a shockable rhythm.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170 and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
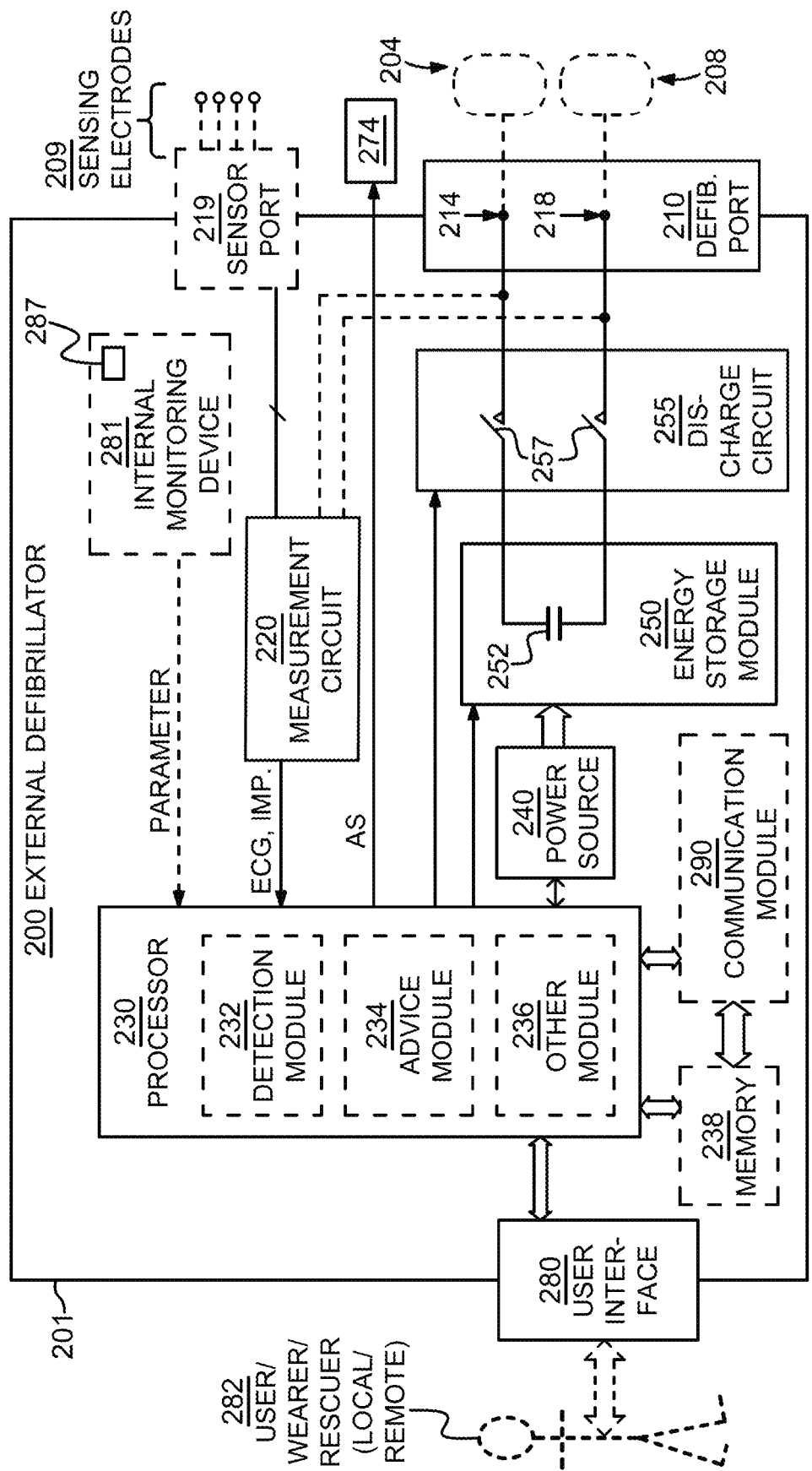
FIG. 2 is a diagram showing sample components of an external defibrillator, made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible, or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touch-screens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the defibrillation electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for defibrillation electrodes 204, 208, and/or for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No. 16/038,007, filed on Jul. 17, 2018 and since published as US 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282 if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as described below in the "Zoneless Arrythmia Detection" section. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include other components.

Figure 3:
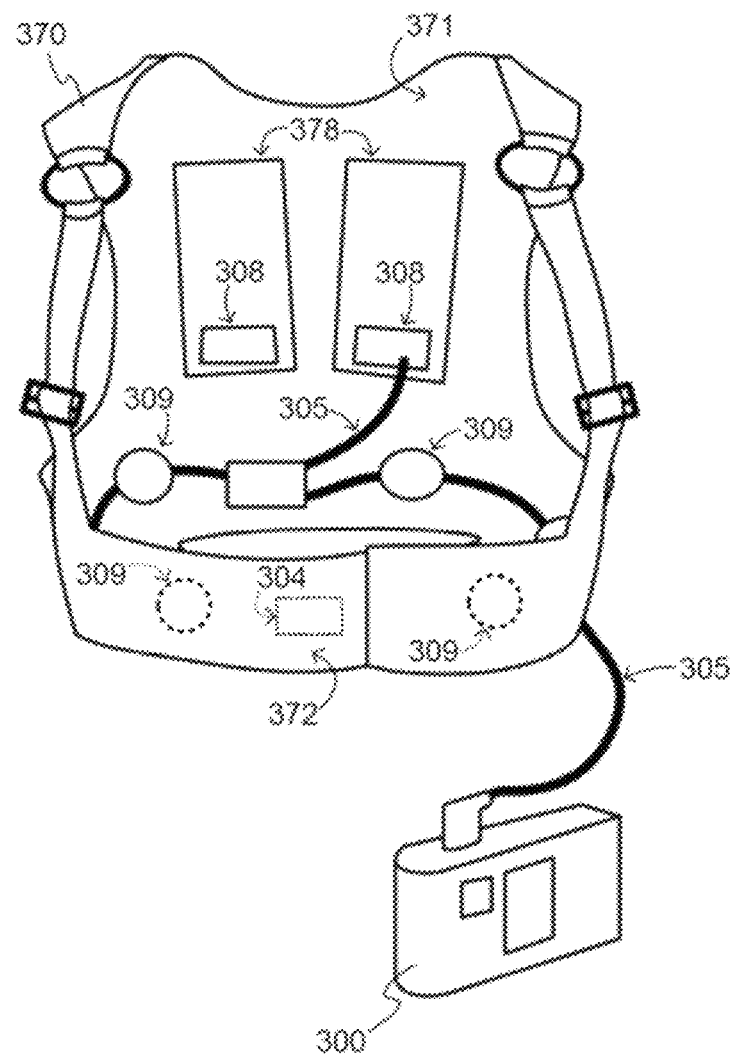
FIG. 3 is a diagram of sample embodiments of components of a WCD system made in accordance with this disclosure.

FIG. 3 is a diagram of sample embodiments of components of an WCD system. A support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with conductive fabric, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 4:
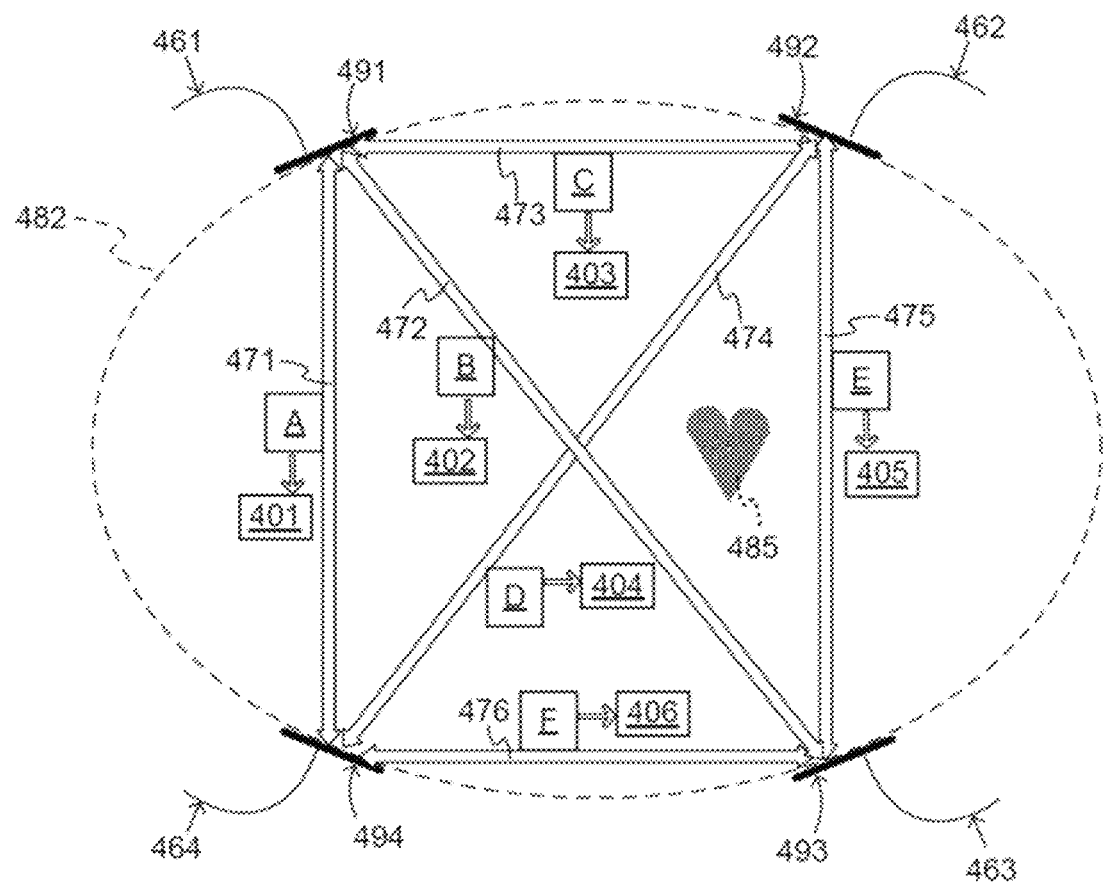
FIG. 4 is a conceptual diagram illustrating how multiple electrodes of a WCD system may be used for sensing ECG signals along different vectors according to embodiments.

FIG. 4 is a conceptual diagram for illustrating how multiple electrodes of a WCD system may be used for sensing ECG signals along different vectors according to embodiments. In FIG. 4, the sizes/shapes/positions of the torso, electrodes and heart are approximate and not to scale. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either.

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to determine the patient's heart rate and/or RR intervals. For example, in some embodiments the aggregation can be implemented as disclosed in U.S. Pat. No. 9,757,581 issued Sep. 12, 2017 entitled "Wearable Cardioverter Defibrillator Components Making Aggregate Shock/No Shock Determination From Two Or More ECG Signals", which is incorporated herein by reference.

Because a WCD is worn by patients, patient movement may cause changes at the electrode-skin interface, resulting in noise on an ECG signal. This noise can be a significant problem by interfering with ECG interpretation.

In embodiments, the WCD device uses four monitoring electrodes which can generate six differential ECG vectors. When the patient wearing the WCE is moving, some ECG electrodes may be more susceptible to movement artifact than others, resulting in some ECG vectors having more noise than other ECG vectors. In embodiments, different assessment methods are used on all of ECG vectors. If the assessments for an ECG vector have similar results, then the ECG vector is deemed reliable. The ECG vectors deemed to be reliable can then be used in a rhythm analysis, resulting in a more accurate result.

In some embodiments in which only a single ECG vector is used, different assessment methods can be used on this single vector, with only portions of the ECG signal that are deemed reliable being used in the rhythm analysis. In an enhancement, the WCD device can be configured to prompt the patient to reduce activity if the number of ECG portions that are deemed unreliable exceeds a threshold. This can reduce the amount of noise generated by the patient's movement and increase the number of ECG portions that are deemed reliable.

Data Channel Selection and Timeline Navigation GUI

Figure 5:
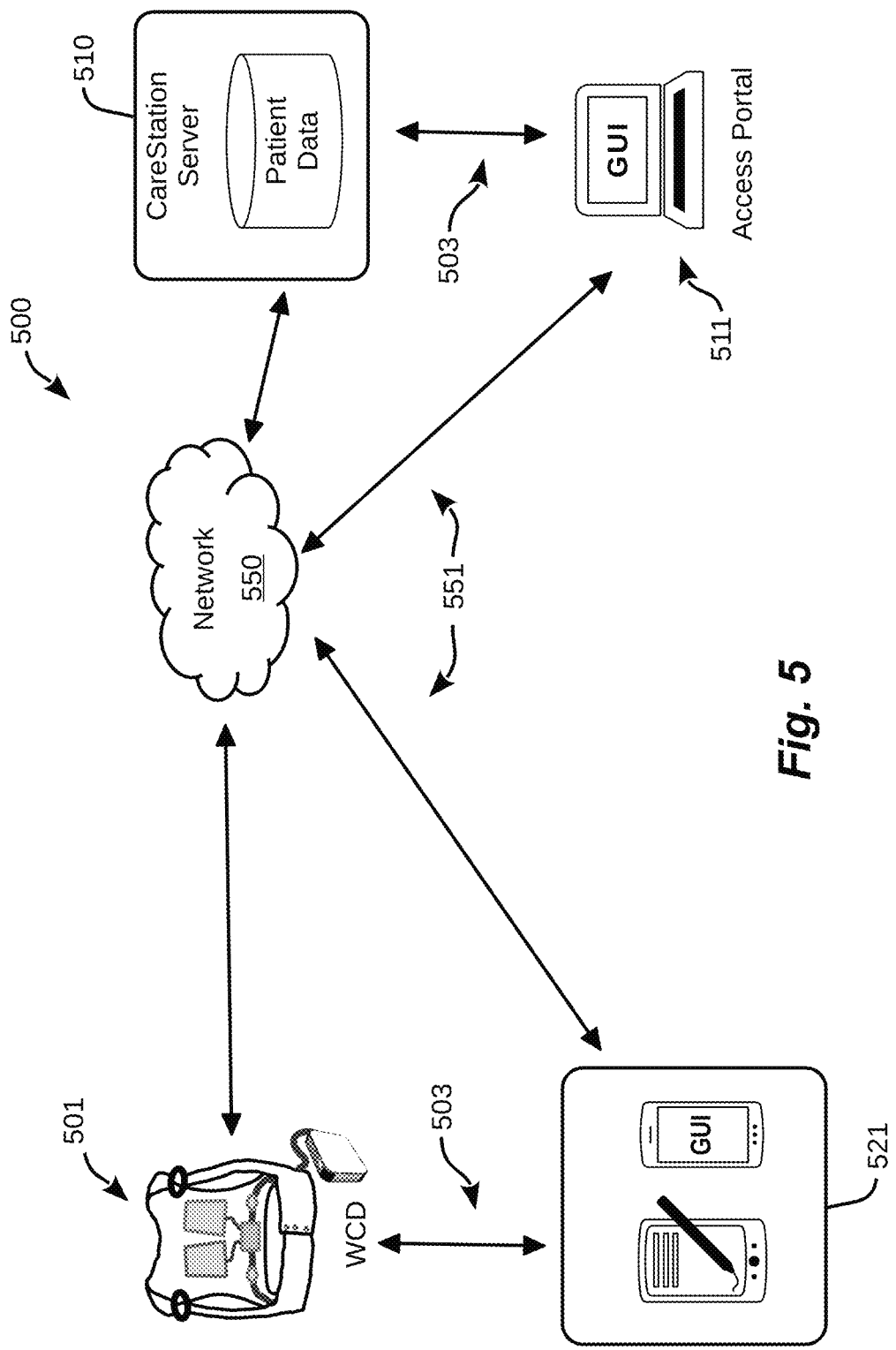
FIG. 5 is a conceptual diagram generally illustrating a cardiac monitoring environment according to embodiments.

Turning now to the second part of the disclosure, FIG. 5 is a conceptual diagram generally illustrating a cardiac monitoring environment 500 according to embodiments. As illustrated in FIG. 5, the cardiac monitoring environment 500 includes a wearable cardiac monitoring device (WCD 501), a mobile device 521, a remote patient data platform (CareStation server 510), and one or more access portals 511. Each of those components variously communicates with one or more of the others either locally over a local communication link 503 or remotely over a remote communication link 551 through a wide area network 550, such as the Internet.

The wearable cardiac monitoring device may be any medical device configured to detect and report on patient physiological parameters, such as described at length above. The wearable cardiac monitoring device is described herein as a WCD 501 for simplicity of discussion only. One example of such a WCD 501 is the Assure WCD developed and offered by Kestra Medical Technologies, Inc. of Kirkland, Wash. Many other types of wearable cardiac monitoring devices may be used in various alternative embodiments without departing from the spirit of the disclosure. Accordingly, reference to use of a WCD 501 as the cardiac monitoring device is illustrative only and is not limiting of the disclosure.

The WCD 501 may also communicate over a local communication link 503 with a mobile device 521 operating a patient application configured to facilitate communication between the WCD 501 and other remote devices. In one example, the mobile device 521 and the WCD 501 may communicate using a relatively short-range local communication link 503, such as Ethernet, Bluetooth, or Wi-Fi. The mobile device 521 may also communicate with other remote devices using a remote communication link 551 to a wide area network 550, such as the Internet. In one specific embodiment, the patient application operating on the mobile device 521 may be the Assure patient app developed and offered by Kestra Medical Technologies, Inc. of Kirkland, Wash. In various embodiments, the patient application operating on the mobile device 521 may provide a graphical user interface (GUI) that enables review of patient physiological parameters captured by the WCD 501. Specific implementations of the GUI are described in greater detail below.

In the preferred embodiment, the remote patient data platform is implemented as a remote server for use by medical professionals, using one or more remote access portals 511, that offers efficient tools for managing cardiac patient care. In various embodiments, the remote patient data platform delivers relevant data and valuable insights into patient heart rhythms and usage compliance by providing clear patient reports that include VT, VF, bradycardia, asystole, and non-sustained ventricular arrhythmia episodes; WCD usage and physical activity trends; and may include a population dashboard with configurable notifications. One example of such a remote patient data platform is the CareStation platform developed and offered by Kestra Medical Technologies, Inc. of Kirkland, Wash. The remote patient data platform is described herein as a CareStation server for simplicity of discussion only. Many other types of remote patient data platforms may be used in various alternative embodiments without departing from the spirit of the disclosure. Accordingly, reference to use of a CareStation server as the remote patient data platform is illustrative only and is not limiting of the disclosure.

In communication with the CareStation server 510, either with a remote communication link 551 over a wide area network 550 or over a local communication link 503 (e.g., a LAN), is one or more access portal(s) 511. Each access portal 511 represents a computing display device that communicates with the CareStation server 510 to interact with and display patient data on a graphical user interface (GUI) as is described in greater detail below. Generally stated, patient data is recorded by the WCD 501 and uploaded, either by the WCD 501 directly or by using an associated mobile device 521, to the CareStation server 510. Medical professionals access that patient data stored on the CareStation server 510 using the access portal(s) 511. The CareStation server 510 stores the patient data and may perform several analyses on the patient data to identify patient health issues, such as the occurrence of arrythmias, shockable and non-shockable events, and other medical events. In addition, after-action evaluations may be performed on the patient data to help improve the quality of future shock therapy.

It should be noted that although the GUI may be illustrated in FIG. 5 as being resident either within the access portal 511 or the mobile device 521, the functional components of the GUI may in fact be stored at the CareStation server 510 and delivered on demand to rendering devices, such as the access portal 511 or the mobile device 521. This and many other alternatives will become apparent from the teachings of this disclosure.

Figure 6:
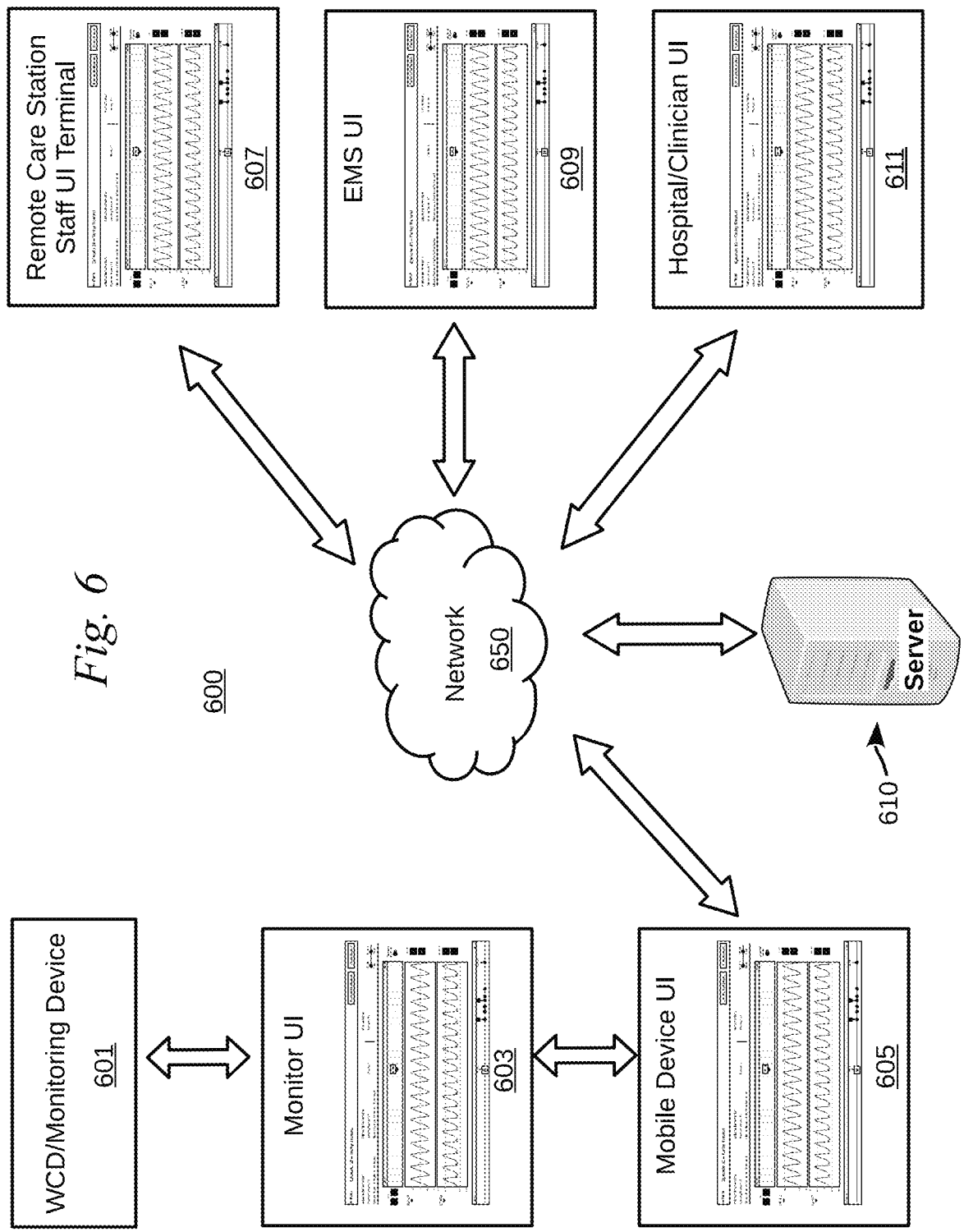
FIG. 6 is a conceptual diagram generally illustrating graphical user interface options used in the cardiac monitoring environment illustrated in FIG. 5.

FIG. 6 is another conceptual illustration of a system 600 that enables different types of users to access patient data through a data channel graphical user interface (GUI) and to select data segments for viewing. The system 600 can include authorized devices to be connected to the network through wired and/or wireless links. For example, in some embodiments the cardiac monitoring system 600 includes a personal communication device (e.g., a smartphone) that communicates with a wearable monitoring device via a short-range wireless link (e.g., Bluetooth), and to a server 610 via a wireless cellular link (e.g., 4G, LTE, 5G). The system 600 can be configured so that patient data (including ECG data) from the cardiac monitoring systems are securely communicated to the server 610.

The display and selection of patient data can be accessed by authorized clients/users, such as EMS, clinicians, etc., using access portals implemented as computers, personal communication devices, smart devices, or the like via the network 650. Each access portal would implement the data channel GUI for presentation of the patient data. For example, a physician for one of the patients could access ECG data of that particular patient from the server 650 using the clinician portal 611. In embodiments of the present disclosure, the GUI can be implemented on a remote CareStation platform and can include a server 610 through which authorized clients/users, for example EMS, clinicians, etc., can access the GUI and the patient data.

In summary, by providing a monitoring system 600 with a GUI configured to allow a user to visually select which data segments the user would like to view, embodiments disclosed herein reduce data overload to an emergency personnel and provide a user with a configuration that allows quick assessment of key events.

Figure 7:
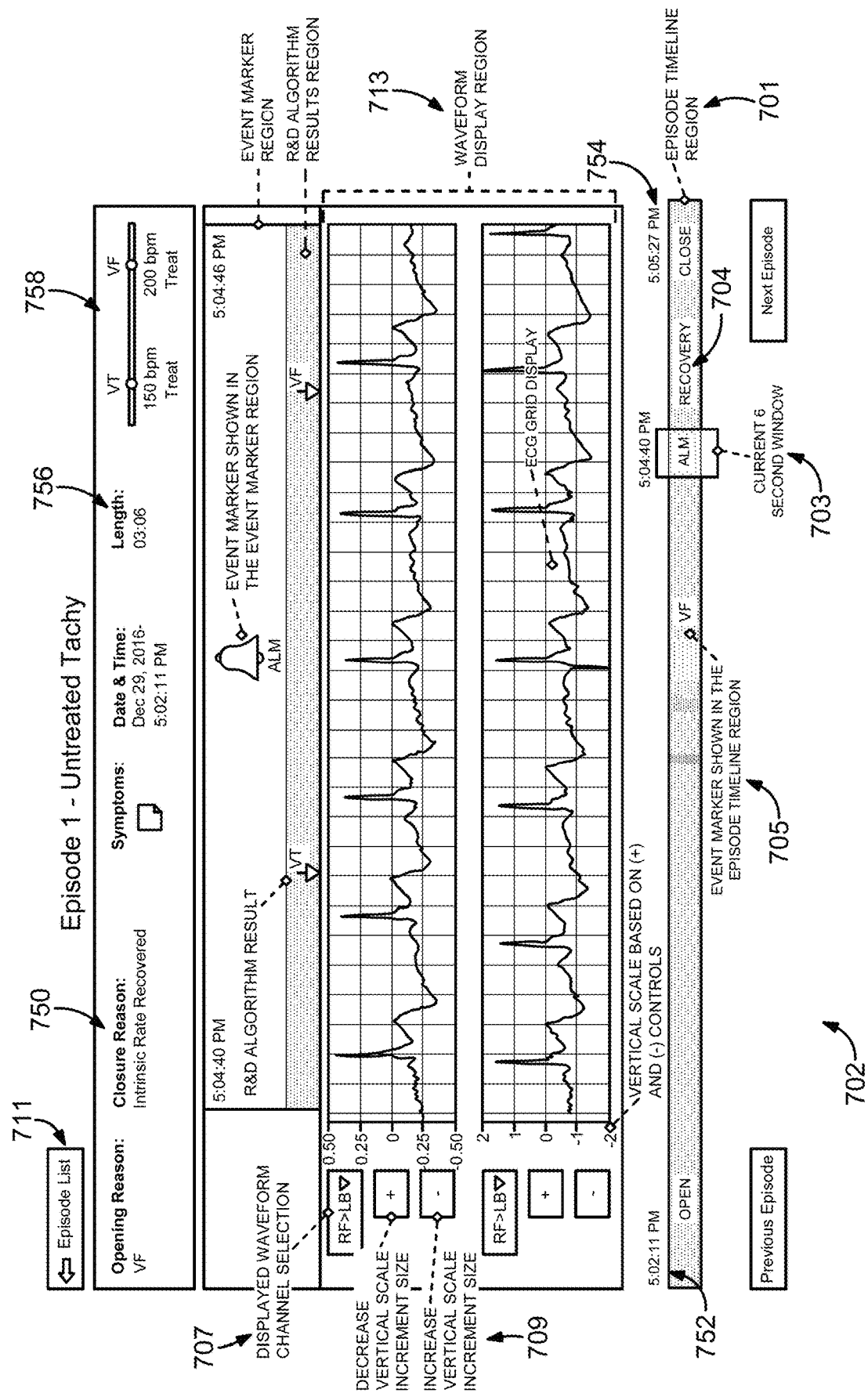
FIG. 7 is an annotated illustration of a first embodiment of a data channel GUI for reviewing patient data in accordance with this disclosure.
Figure 8:
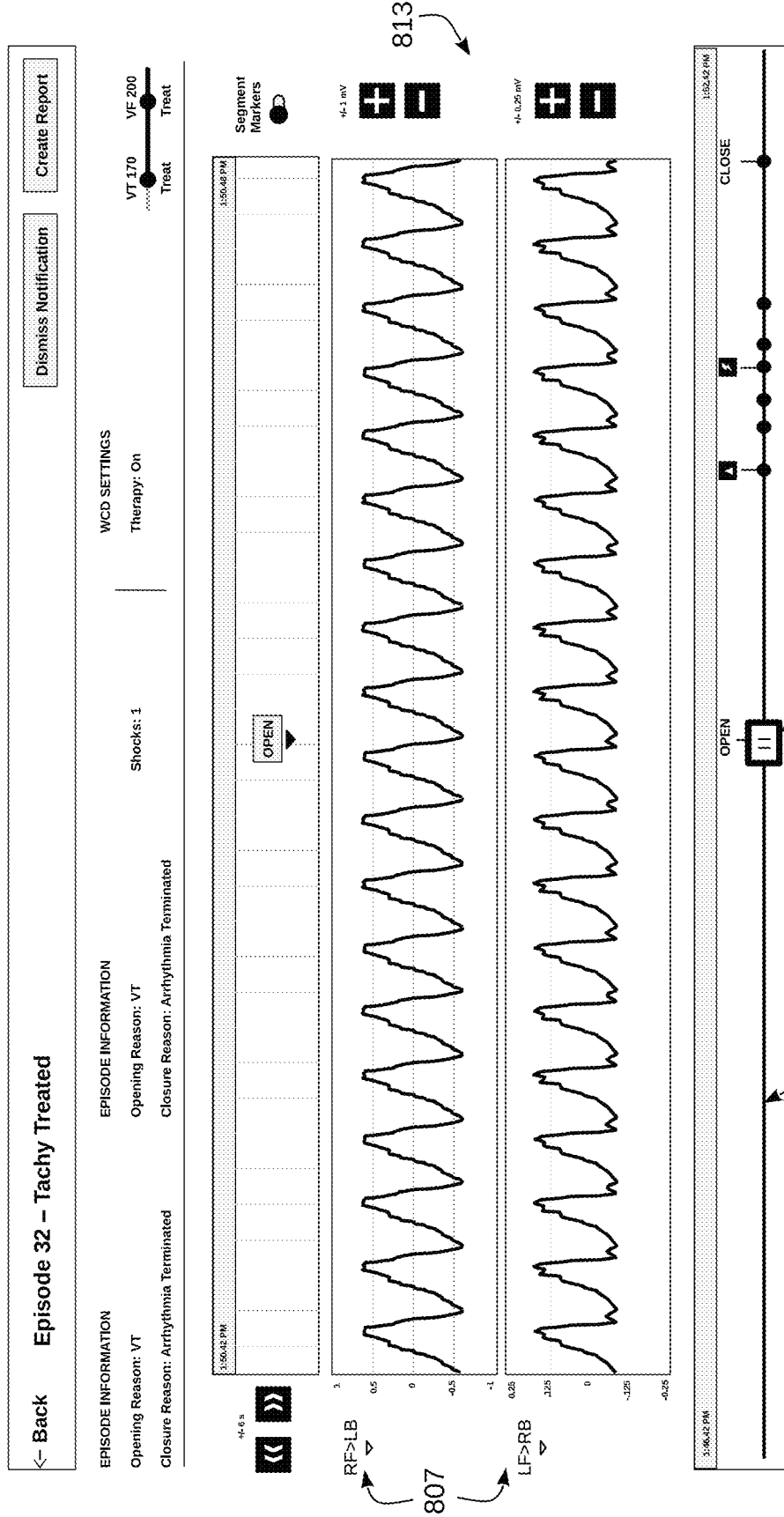
FIG. 8 is an illustration of another embodiment of a data channel GUI for reviewing patient data in accordance with this disclosure.

Turning now to FIGS. 7 and 8, illustrated are specific implementations of a data channel graphical user interface (GUI) that may be employed in various embodiments to enable medical personnel to better evaluate collected patient data. In the preferred embodiment, a WCD is configured to collect patient data using plural ECG sensing channels as described above with respect to FIG. 4. In various embodiments of the GUI, the patient data collected from each channel can be displayed within its respective channel.

Before continuing, it may be helpful to clarify certain terminology that will be used below. The following description refers to "episodes" and "events" in patient data. As used below, the term "event" refers to either the occurrence of an abnormality in one or more of a patient's physiological parameters or a therapeutic response to such an abnormality. For instance, a patient may experience the occurrence of some form of heart arrhythmia, such as a tachycardia, or bradycardia. An acute instance of that arrhythmia may be deemed an event. Events may include, for example, any ECG trace that departs from a patient's normal ECG, which could indicate serious cardiac conditions such as ventricular fibrillation, ventricular tachycardia, atrial arrhythmia, atrial fibrillation, supraventricular tachycardia, premature ventricular contraction, and the like. In addition, in some instances, a therapeutic shock may be delivered to address a detected cardiac event, such as ventricular fibrillation. The delivery of that therapeutic shock may also be considered an event for the purposes of this discussion.

It will be appreciated that a patient may experience, and often does experience, multiple related events over a short period of time. For example, a patient may experience a ventricular fibrillation "event" followed almost immediately by delivery of a therapeutic shock "event" to try and remedy the ventricular fibrillation. Those two events would be considered part of the same "episode" for purposes of the following description. Similarly, a second or possibly even third therapeutic shock may be delivered before the ventricular fibrillation was remedied. All of those events would be considered part of the same episode for purposes of this discussion. Accordingly, an "episode" may include one "event" or multiple related "events" over some period of time.

In operation, the occurrence of a first event may trigger recording patient data as an episode surrounding that first event and any subsequent related events so that the related events may be later reviewed and analyzed together. ECG signal(s) associated with the detected event are recorded along with optionally other physiological parameters that can supplement and/or support the occurrence of an event and aid analysis. Episodes of patient data can be stored on the monitoring device and transferred to a remote location.

Turning now to the drawings, FIG. 7 is an annotated illustration of a first embodiment of a data channel GUI 700 for reviewing patient data in accordance with this disclosure. As illustrated in FIG. 7, the GUI 700 may be rendered on any device with access to the patient data, either locally or remotely, such as the access portal 511 or the mobile device 521 (see FIG. 5). The example illustrated in FIG. 7 may represent an untreated episode of cardiac arrhythmia, such as tachycardia. The GUI 700 provides a visual representation of patient data so that a user can evaluate the patient's heart rhythm over time.

The embodiment of GUI 700 as shown in FIG. 7 includes two channel display regions 713 that each renders patient data (e.g., an ECG trace) from a respective patient data channel that is user-selectable with channel controls 707. In one embodiment, the GUI 700 is configured to allow selection, using channel controls 707, of a one or more channels of patient data for simultaneous display. This feature enables a user to focus on selected, pertinent data without tasking the user's attention with extraneous data. As noted above, a WCD 501 (FIG. 5) may be configured to capture four different channels of patient data. Accordingly, in the embodiment of GUI 700 shown in FIG. 7, any two of those four channels may be selected for display. In alternative embodiments, additional display regions 713 may be included to display more data channels. In still other embodiments, one or more of the display regions 713 may be selectively "turned off" or hidden to further limit extraneous data tasking the user's vision.

In other embodiments, patient physiological data other than an ECG trace could be used, such as accelerometer data channel, impedance, pacing, respiration, heart rate, pulse oxygenation, time-correlated data channels from the same and/or other devices, etc. Still other data channels could include physiologic and/or equipment data channels, such as ECG electrode contact status. In this way, a patient's ECG trace may be visually compared to another of the patient's physiological parameters (e.g., blood oxygen level) simultaneously for analysis or other purposes.

As illustrated in FIG. 7, the patient data being rendered to the GUI 700 represents a roughly three-minute episode as shown in the episode timeline region 701. Of that episode, an approximately six-second window—identified by a scrubber 703 on the episode timeline region—of channel data (ECG trace data in this example) is rendered by the GUI 700. The episode timeline region 701 also includes icons or event markers (e.g., marker 705) that indicate the occurrence of one or more identified events and visually when during the episode those events occurred. In addition, a recovery marker 704 may indicate when along the timeline 701 recovery occurred.

The timeline region 701 (also referred to as a timeline navigation bar) and scrubber 703 enable timeline-based navigation of the episode so a user can quickly identify, by visual assessment, significant events and quickly navigate to those sections of the episode for analysis of the patient data. Such features enable expedited assessment of key events throughout a larger, or entire, period of data and quick navigation to those events of highest interest. For example, a user could quickly and visually determine whether a shock had been delivered during an episode and immediately advance the detailed display of data 713 to that point in the episode by sliding the scrubber 703 along the timeline region 701).

In some embodiments, the GUI 700 includes scale controls 709 to enable a user to increase and/or decrease the scale/size of the ECG segment 713. In a further embodiment, the GUI 700 is configured to enable a user to zoom in and zoom out on a displayed segment.

Further embodiments of the GUI 700 can be configured to enable a user to navigate between episodes, or return to an episode list 711. The episode list 711 enables a user to graphically select a particular episode. In one embodiment, the GUI enables a user to navigate to an episode based on events within the timeline. For example, some episodes can close as a new episode opens, and the timeline can be used to navigate directly to the new episode.

Still other information that may be available in the GUI 700 includes the reasons 750 for opening and closing the episode; the times when the episode were opened 752 and closed 754; the length of the episode 756, and thresholds of VT and VF seen during the episode 758. In some embodiments, the remote monitoring system is configured to enable a user to see if any symptoms were recorded by, for example clicking on the "Symptoms" icon.

FIG. 8 is an illustration of another embodiment of a data channel GUI 800 for reviewing patient data in accordance with this disclosure. As with the GUI 700 illustrated in FIG. 7, the GUI 800 includes an interactive user interface with a timeline region 801 (also referred to as a timeline navigation bar) and channel display regions 813. The GUI 800 allows a user to navigate along the timeline region 801 by sliding a scrubber 803 along the timeline to select the appropriate portion of the episode to review. In addition, the user may select the desired channel data for display using channel controls 807. In this way, the patient data (e.g., ECG waveform data) corresponding to the selected channels may be displayed in the channel display regions 813 for the corresponding portion of the episode identified by the scrubber 803 on the timeline 801.

As shown in FIG. 8, the GUI 800 displays an episode of a tachycardia event according to embodiments of the disclosure. The scrubber 803 indicates a selected time period along the timeline corresponding to the data being displayed by the GUI 800. In some embodiments, the GUI 800 is touch aware so that the user can tap on any point along the timeline region 801 to cause the GUI 800 to display a portion of the ECG corresponding to the tapped point. In that way, a user can tap anywhere on the timeline 801 to move the current six seconds of data being displayed to that point in the current episode. The timeline region 801 also includes markers to indicate significant events to help the user quickly navigate through the data.

Other embodiments include combinations and sub-combinations of features described or shown in the drawings herein, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

The embodiments of the disclosure in which an exclusive property or privilege is claimed are recited as follows:

1. A system for displaying patient data captured by a wearable monitoring device, the system comprising:
    a data storage component on which are stored computer executable components;
    a display device; and
    a processor configured to execute the computer executable components and to cause images to be displayed on the display device, the computer executable components including:
        a graphical user interface (GUI) configured to render on the display device:
            a timeline region corresponding to an episode captured by the wearable monitoring device, the episode comprising patient data describing one or more events, the timeline region including one or more event markers, each event marker corresponding to the one or more events,
            a scrubber element on the timeline region, the scrubber element being configured to identify a selected section of the timeline region, the selected section being a subset of the episode,
            first patient data corresponding to the selected section, the first patient data further corresponding to a selected channel, the first patient data being displayed within a channel region of the GUI, and
            a recovery marker configured to indicate when a recovery of a patient from the one or more events occurred along the timeline region.

2. The system recited in claim 1, wherein the GUI is further configured to display second patient data corresponding to the selected section, the second patient data corresponding to a second selected channel.

3. The system recited in claim 2, wherein the first and second patient data correspond to first and second Electrocardiogram (ECG) channels captured by the wearable monitoring device.

4. The system recited in claim 1, wherein the wearable monitoring device comprises a wearable cardioverter defibrillator (WCD).

5. The system recited in claim 1, wherein the display device is associated with a remote device communicatively coupled to the data storage component over a network.

6. The system recited in claim 1, wherein the first patient data comprises Electrocardiogram (ECG) waveform data.

7. The system recited in claim 1, wherein the first patient data is retrieved over a network from a remote patient data platform.

8. A method, comprising:
    displaying, by a graphical user interface (GUI), a timeline comprising one or more markers of events that occurred during an episode captured by a wearable monitoring device;
    displaying, by the GUI, a first section of a first electrocardiogram (ECG) waveform, the first section corresponding to a first portion of the timeline;
    receiving, by the GUI, a user selection of a second portion of the timeline; and
    displaying, by the GUI, a second section of the first ECG waveform, the second section corresponding to the second portion of the timeline.

9. The method of claim 8, further comprising displaying, by the GUI, a section of a second ECG waveform concurrently with the first section of the first ECG waveform, the first section of the first ECG waveform and the section of the second ECG waveform corresponding to the first portion of the timeline.

10. The method of claim 9, wherein the first and second ECG waveforms correspond to first and second ECG channels captured by the wearable monitoring device.

11. The method of claim 8, wherein the wearable monitoring device comprises a wearable cardioverter defibrillator (WCD).

12. The method of claim 8, wherein the GUI is implemented on a remote device communicatively coupled to the wearable monitoring device.

13. The method of claim 8, further comprising automatically displaying, by the GUI, a most recent episode.

14. A system for displaying patient data captured by a wearable monitoring device, the system comprising:
- a data storage component on which are stored computer executable components;
- a display device; and
- a processor configured to execute the computer executable components and to cause images to be displayed on the display device, the computer executable components including:
  - a graphical user interface (GUI) configured to render on the display device:
    - a timeline region corresponding to an episode captured by the wearable monitoring device, the episode comprising patient data describing one or more events, the patient data comprising a plurality of channel data, the timeline region including one or more event markers, each event marker corresponding to the one or more events,
    - a first channel region in which is displayed a first ECG waveform corresponding to a first channel data of the patient data, the first channel region comprising a first channel selection control, and
    - a second channel region in which is displayed a second ECG waveform corresponding to a second channel data of the patient data, the second channel region comprising a second channel selection control;
    - wherein the first channel data and the second channel data correspond to a same portion of the timeline region.

15. The system recited in claim 14, wherein the GUI is further configured to render in the first channel region a third ECG waveform corresponding to a third channel data of the patient data.

16. The system recited in claim 15, wherein the first channel selection control is configured to cause the first channel region to change from the first ECG waveform to the third ECG waveform.

17. The system recited in claim 14, wherein the wearable monitoring device comprises a Wearable Cardioverter Defibrillator (WCD).

18. The system recited in claim 14, wherein the GUI is further configured to render on the display device a scrubber in association with the timeline region, the scrubber being configured to enable a selection of a different portion of the timeline region for display.

19. The system recited in claim 14, wherein the patient data comprises patient physiological data in addition to ECG waveform data.

20. The system of claim 1, wherein the first patient data corresponds to Electrocardiogram (ECG) waveform data and at least one physiological parameter of the patient, and wherein the first patient data corresponding to the ECG waveform data is visually compared with the first patient data corresponding to the at least one physiological parameter of the patient simultaneously on the GUI of the display device.

* * * * *